United States Patent
Voss (10) Patent No.: US 8,740,938 B2
(45) Date of Patent: Jun. 3, 2014

(54) SYSTEM, METHOD, AND DEVICE FOR CLOSING AN OPENING

(75) Inventor: Laveille K. Voss, Belmont, CA (US)

(73) Assignee: Abbott Laboratories, Abbott Park, IL (US)

( * ) Notice: Subject to any disclaimer, the term of this patent is extended or adjusted under 35 U.S.C. 154(b) by 1021 days.

(21) Appl. No.: 12/335,102

(22) Filed: Dec. 15, 2008

(65) Prior Publication Data

US 2009/0157100 A1  Jun. 18, 2009

Related U.S. Application Data (60) Provisional application No. 61/014,718, filed on Dec. 18, 2007.

(51) Int. Cl.
*A61B 17/04* (2006.01)

(52) U.S. Cl.
USPC .......................................... 606/232; 606/139

(58) Field of Classification Search
CPC .................................................. A61B 17/0487
USPC ................. 606/139–147, 151–158, 213, 232; 623/23.72; 128/831, 843
See application file for complete search history.

(56) References Cited

U.S. PATENT DOCUMENTS

| | | | |
|---|---|---|---|
| 5,531,759 A * | 7/1996 | Kensey et al. | 606/213 |
| 5,855,586 A * | 1/1999 | Habara et al. | 606/144 |
| 6,409,743 B1 | 6/2002 | Fenton, Jr. | |
| 7,883,538 B2 * | 2/2011 | To et al. | 623/2.11 |
| 2003/0125767 A1 | 7/2003 | Collier et al. | |
| 2003/0167071 A1 * | 9/2003 | Martin et al. | 606/232 |
| 2006/0241656 A1 | 10/2006 | Starksen et al. | |
| 2007/0049970 A1 | 3/2007 | Belef et al. | |

FOREIGN PATENT DOCUMENTS

WO  WO 03/073913  9/2003
WO  WO 2009/079513  6/2009

OTHER PUBLICATIONS

U.S. Appl. No. 61/014,718, filed Dec. 15, 2008, Voss.

* cited by examiner

*Primary Examiner* — Melanie Tyson
(74) *Attorney, Agent, or Firm* — Workman Nydegger; Randy Shen (57) ABSTRACT

Disclosed are systems, methods, and devices for closing an opening. The methods, systems, and devices include a looped body. The looped body includes a first looped portion having a first apex and a second apex separated by a first distance while the looped body is in a pre-deployed state. The first looped portion is configured to resiliently move to a deployed state in which the first apex and the second apex are separated by a second distance, the first distance being greater than the second distance.

19 Claims, 5 Drawing Sheets

SYSTEM, METHOD, AND DEVICE FOR CLOSING AN OPENING

CROSS-REFERENCE TO RELATED APPLICATIONS

This application claims the benefit of and priority to U.S. Provisional Patent Application No. 61/014,718, filed Dec. 18, 2007, and entitled "System, Method and Device for Closing an Opening" which is incorporated herein by reference in its entirety.

BACKGROUND

1. Field of the Invention

The present invention relates generally to systems, methods, and devices for closing an opening. More particularly, the present invention relates to techniques for percutaneous closure of arterial and venous puncture sites, which are usually accessed through a tissue tract.

2. Relevant Technology

A number of diagnostic and interventional vascular procedures are now performed translumenally. A catheter is introduced to the vascular system at a convenient access location and guided through the vascular system to a target location using established techniques. Such procedures require vascular access, which is usually established during the well-known Seldinger technique, as described, for example, in William Grossman's Cardiac Catheterization and Angioplasty, 3$^{rd}$ Ed., Lea and Febiger, Philadelphia, 1986, incorporated herein by reference. Vascular access is generally provided through an introducer sheath, which is positioned to extend from outside the patient body into the vascular lumen.

When vascular access is no longer required, the introducer sheath is removed, and bleeding at the puncture site is stopped. One common approach for providing hemostasis (the cessation of bleeding) is to apply external force near and upstream from the puncture site, typically by manual or digital compression. This approach suffers from a number of disadvantages. It is time consuming, frequently requiring one-half hour or more of compression before hemostasis is assured. Additionally, such compression techniques rely on clot formation, which can be delayed until anticoagulants used in vascular therapy procedures (such as for heart attacks, stent deployment, non-optical PTCA results, and the like) wear off. This can take two to four hours, thereby increasing the time required before completion of the compression technique. The compression procedure is further uncomfortable for the patient and frequently requires analgesics to be tolerable. Moreover, the application of excessive pressure can at times totally occlude the underlying blood vessel, resulting in ischemia and/or thrombosis. Following manual compression, the patient typically remains recumbent from four to as much as 12 hours or more under close observation so as to assure continued hemostasis. During this time renewed bleeding may occur, resulting in blood loss through the tract, hematoma, and/or pseudo-aneurysm formation, as well as arteriovenous fistula formation. These complications may require blood transfusion and/or surgical intervention.

The incidence of complications from compression-induced hemostasis increases when the size of the introducer sheath grows larger, and/or when the patient is anti-coagulated. It is clear that the compression technique for arterial closure can be risky and is expensive and onerous to the patient. Although the risk of complications can be reduced by using highly trained individuals, dedicating such personnel to this task is both expensive and inefficient. Furthermore, as the number and efficacy of translumenally performed diagnostic and interventional vascular procedures increases, the number of patients requiring effective hemostasis for a vascular puncture also increases.

To overcome the problems associated with manual compression, the use of bioabsorbable fasteners or sealing bodies to stop bleeding has previously been proposed. Generally, these approaches rely on the placement of a thrombogenic and bioabsorbable material, such as collagen, at the superficial arterial wall over the puncture site. While potentially effective, this approach suffers from a number of problems. It can be difficult to properly locate the interface of the overlying tissue and the adventitial surface of the blood vessel. Locating the fastener too far from that interface can result in failure to provide hemostasis, and subsequent hematoma and/or pseudo-aneurysm formation. Conversely, if the sealing body intrudes into the artificial lumen, intravascular clots and/or collagen pieces with thrombus attached can form and embolize downstream, causing vascular occlusion. Also, thrombus formation on the surface of a sealing body protruding into the lumen can cause a stenosis, which can obstruct normal blood flow. Other possible complications include infection, as well as adverse reaction to the collagen or other implant.

A more effective approach for vascular closure has been proposed in U.S. Pat. Nos. 5,417,699, 5,613,974, and PCT published Patent Application No. PCT/US96/10271 filed on Jun. 12, 1996, the full disclosures of which are incorporated herein by reference. A suture-applying device is introduced through the tissue tract with a distal end of the device extending through the vascular puncture. One or more needles in the device are then used to draw the suture through the blood vessel wall on opposite sides of the puncture, and the suture is secured directly over the adventitial surface of the blood vessel wall to provide highly reliable closure.

Frequently, a suture is fastened with knots. Such knots are often tied proximally and then advanced into proximity with the blood vessel where the knots are tightened to secure a suture. Securing a suture maintains the apposition provided above to maintain hemostasis. Sometimes, however, tying knots can be a time consuming process.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

A suture-fastening device is provided herein that includes a looped body. The looped body includes a first looped portion having a first apex and a second apex separated by a first distance while the suture-fastening device is in a pre-deployed state. The first looped portion is configured to resiliently move to a deployed state in which the first apex and the second apex are separated by a second distance, the first distance being greater than the second distance.

A system is provided herein for maintaining apposition in a suture. The system includes a deployment device, the deployment device having a housing and an actuator assembly. The system also includes a suture-fastening device. The suture-fastening device includes a looped body, the looped body having a first looped portion having a first and a second apex separated by a first distance while the suture maintaining device is in a pre-deployed state and is configured to resiliently move to a deployed state in which the first and second apexes are separated by a second distance, the first distance being greater than the second distance. The deployment device is configured to move the suture-fastening device from the pre-deployed position to the deployed position.

A method of securing a suture in tissue is provided that includes placing a suture-fastening device in a pre-deployed state. The suture-fastening device includes a looped body, the looped body having a first looped portion having a first and a second apex separated by a first distance while the suture-fastening device is in the pre-deployed state and being configured to resiliently move to a deployed state in which the first and second apexes are separated by a second distance, the first distance being greater than the second distance. The method also includes threading ends of the suture through the suture-fastening device and moving the suture-fastening device to the deployed state.

Additional features and advantages will be set forth in the description that follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

In order to describe the manner in which the above recited and other advantages and features can be obtained, a more particular description of the subject matter briefly described above will be rendered by reference to specific embodiments that are illustrated in the appended drawings. Understanding that these drawings depict only typical embodiments of the invention and are not, therefore, to be considered to be limiting of its scope, embodiments will be described and explained with additional specificity and detail through the use of the accompanying drawings in which.

DETAILED DESCRIPTION

Methods, devices, and systems are provided herein for securing a suture. In at least one example, a suture-fastening device can be used to retain and/or provide apposition for a suture that has been deployed to close an opening in tissue. The suture-fastening device includes at least a distal loop portion that moves from an expanded state having a first diameter to a constricted state having a second diameter, the second diameter being less than the first. In at least one example, the closure device also includes a proximal loop portion. The suture-fastening device may be moved from a single loop configuration in an expanded state to a configuration that includes a proximal loop and a constricted distal loop in a constricted state. In another example, a suture-fastening device is provided in which the diameter of a distal loop decreases while the diameter of a proximal loop increases as the suture-fastening device is deployed.

Figure 1A:
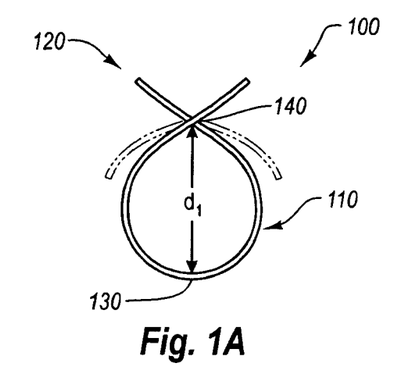
FIG. 1A illustrates a suture-fastening device in a pre-deployed state according to one example.
Figure 1B:
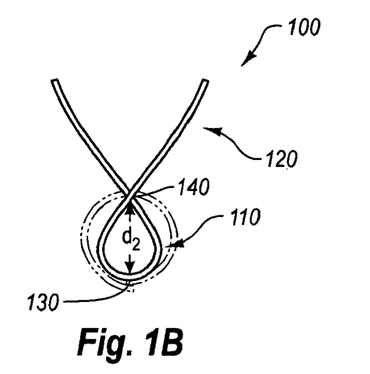
FIG. 1B illustrates the suture-fastening device of FIG. 1A in a deployed state.

FIGS. 1A and 1B illustrate a schematic representation of a suture-fastening device 100 that includes a looped portion 110, such as a distal loop. The suture-fastening device 100 may also include a second portion 120, such as a proximal portion. Details of the second portion 120 have been removed for simplicity of the discussion of the general operation of the suture-fastening device 100. The suture-fastening device 100 illustrated includes a generally circularly-shaped looped portion 110. Although the generally circular shape is illustrated for ease of reference only, it will be appreciated that other shapes and configurations may also be utilized.

The suture-fastening device 100 moves between an expanded state illustrated in FIG. 1A to a constricted state illustrated in FIG. 1B. For ease of reference, the size of the looped portion 110 may be described with reference to a distance between a first apex 130 of the looped portion 110, such as a distal apex, and a second apex 140, such as an apex adjacent the second portion 120.

As illustrated in FIGS. 1A and 1B, the distance $d_1$ between the apexes 130, 140 when the suture-fastening device 100 is in the expanded state is larger than the distance $d_2$ between the apexes 130, 140 when the suture-fastening device 100 is in the constricted state. As will now be discussed in more detail, such a configuration allows the suture-fastening device 100 to secure and/or provide apposition for a suture. As illustrated in FIGS. 1A and 1B, in one example, shown in solid lines, the second portion 120 may extend away from the first apex 130 and the second apex 140. In other examples, illustrated in dashed lines, the second portion 120 may extend back toward the first apex 130, such as to coil back toward the first apex 130. The second portion 120 may further extend past the first apex 130 and/or coil back again toward the second apex 140. The first and second portions 110, 120 may be formed of a single continuous piece of material or may be formed of multiple pieces which are joined together. Further, in the case of a single continuous piece of material, the material may be formed integrally as one or more looped portions or may be formed with multiple ends that are then joined together to form a single continuous piece. Any suitable material may be used, including, without limitation, shape memory materials, resilient materials and/or bio-resorbable materials.

Figure 2A:
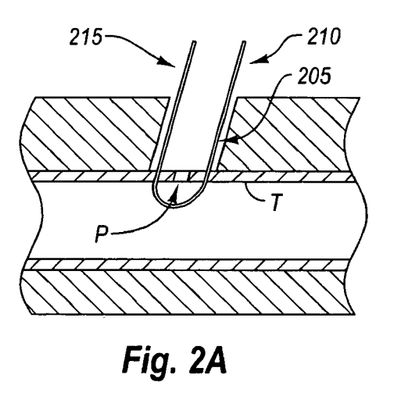
FIG. 2A illustrates a suture deployed in tissue to bring opposing sides of a puncture into apposition.

FIG. 2A illustrates tissue T that has a puncture or opening therein. In the example illustrated, the tissue T defines a body lumen having a puncture P therein. The example of a puncture in a body lumen is provided for ease of reference only.

As illustrated in FIG. 2A, suture 205 passes through tissue T on either side of the puncture P. Ends 210, 215 extend proximally from the tissue T. By applying tension to the ends 210, 215, opposing edges of the puncture P may be brought into apposition.

Figure 2B:
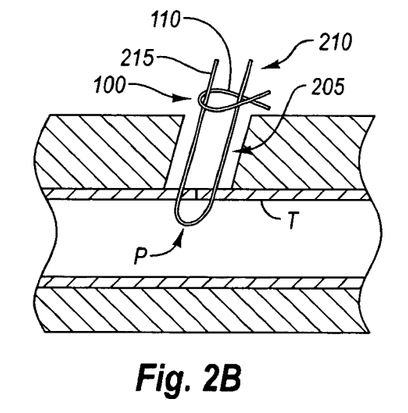
FIG. 2B illustrates ends of the suture threaded through a suture-fastening device according to one example.

In at least one example illustrated in FIG. 2B, the ends 210, 215 of suture 205 may be threaded through the suture-fastening device 100. In particular, the ends 210, 215 may be threaded through the looped portion 110 of the suture-fastening device 100. In at least one example, a deployment device (not shown) may be used to place the looped portion 110 in the expanded state illustrated in FIG. 2B. A deployment device has been omitted to focus on the generalized principles of operation of the suture-fastening device 100. Exemplary deployment devices will be discussed in more detail later.

Figure 2C:
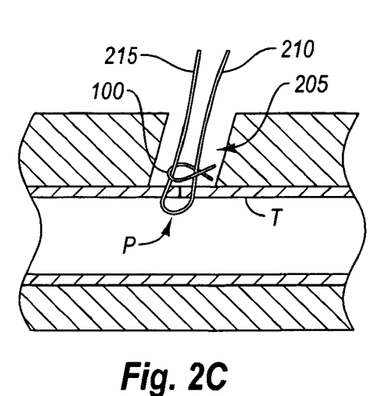
FIG. 2C illustrates the suture-fastening device in proximity with the tissue according to one example.

After ends 210, 215 have been threaded through the looped portion 110, the suture-fastening device 100 may be advanced distally until the suture-fastening device 100 moves into proximity with the puncture P, as illustrated in FIG. 2C.

Figure 2D:
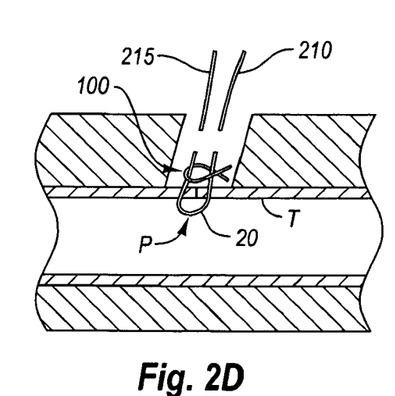
FIG. 2D illustrates the ends of the suture being trimmed proximally of the suture-fastening device.

Once the suture-fastening device 100 is in proximity with the puncture P, the suture-fastening device 100 may be deployed, as illustrated in FIG. 2D. Deploying the suture-fastening device 100 includes moving the looped portion 110 to the constricted state illustrated in FIG. 2C. As the looped portion 110 moves to the constricted state, the looped portion 110 engages the suture 205 proximate to the puncture P. In at least one example, this engagement maintains tension applied to the suture 205 and/or the ends 210, 215 to provide and/or maintain apposition of the tissue T on either side of the puncture P.

After the suture-fastening device 100 has been deployed to engage the suture 205, the ends 210, 215 may be trimmed proximal of the suture-fastening device 100 as shown in FIG. 2D. Accordingly, the suture-fastening device 100 may be deployed to provide and/or maintain tension in a suture and/or maintain apposition between opposing sides of a puncture. To this point the discussion of the operation, deployment, and function of the suture-fastening device 100 has been discussed generally. Two exemplary systems will now be described that include suture-fastening devices and deployment devices.

Figure 3:
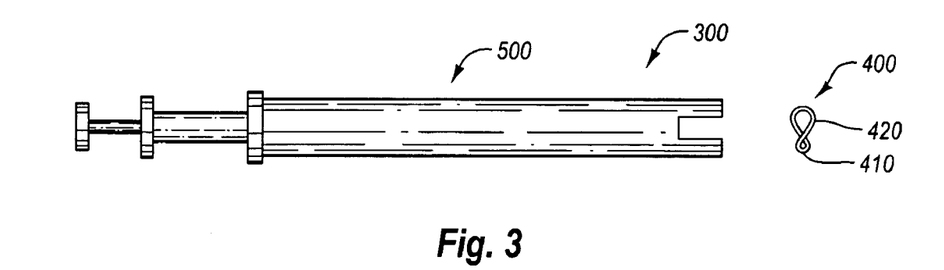
FIG. 3 illustrates a system for retaining a suture according to one example.

FIG. 3 is a perspective view of a system 300 for maintaining tension in a suture for providing and/or maintaining apposition in a puncture in tissue. The system 300 generally includes a suture-fastening device 400 and a deployment device 500. In the illustrated example, the suture-fastening device 400 has a proximal loop portion 420 and a distal loop portion 410 that are in communication with each other. The suture-fastening device 400 will first be discussed with reference to FIGS. 4A and 4B, followed by a discussion of the cooperation between the suture-fastening device 400 and the deployment device 500 in deployment of the suture-fastening device 400 as shown in FIGS. 5A-5D.

Figure 4A:
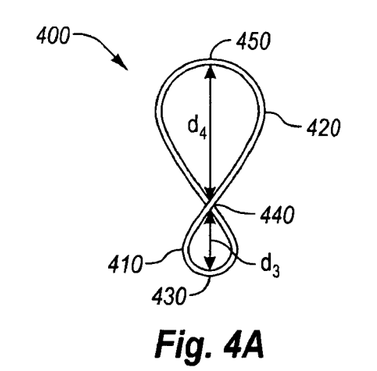
FIG. 4A illustrates a suture-fastening device in a pre-deployed state.

FIG. 4A illustrates the distal loop portion 410 of the suture-fastening device 400 in a pre-deployed state. Such a state may be referred to as a default state or a stressed state. The distal loop portion 410 includes a distal apex 430 as well as a central apex 440. The proximal loop portion 420 includes a proximal apex 450. In the illustrated example, the distal loop portion 410 and the proximal loop portion 420 may be formed of a substantially continuous piece of material. Accordingly, the distal loop portion 410 and the proximal loop portion 420 can both include the central apex 440.

The distal apex 430 and the central apex 440 are separated by a distance referred to as $d_3$ while the central apex 440 and the proximal apex 450 are separated by a distance referred to as $d_4$. The distances $d_3$ and $d_4$ are provided for ease of illustration only and not by way of limitation. In the default state, distance $d_3$ between the distal apex 430 and the central apex 440 may be less than distance $d_4$ between the proximal apex 450 and the central apex 440.

In the illustrated example the distal loop portion 410 and the proximal loop portion 420 are formed from a single continuous piece. A central portion of the looped body may have an overlapping configuration at the second central apex with one portion of the looped body transversely crossing another portion of the looped body. For instance, the suture-fastening device 400 can be cut or removed from a single piece of material as a generally circular or ovular configuration and then be heat set or annealed to transition from the configuration illustrated in FIG. 4A to that of FIG. 4B. As a result, a change in the size of one of the loop portions results in a change in size of the other loop portion as will be discussed in more detail below.

Figure 4B:
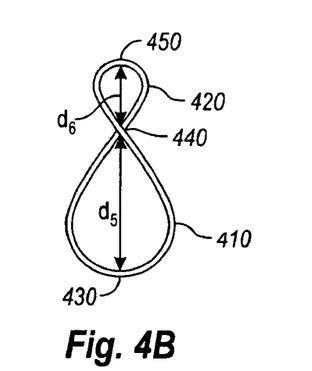
FIG. 4B illustrates the suture-fastening device of FIG. 4A in a deployed state.

FIG. 4B illustrates the suture-fastening device 400 in a state in which proximal loop portion 420 is constricted while the distal loop portion 410 is expanded. In such a state, the distance $d_5$ between the distal apex 430 and the central apex 440 is greater than the distance $d_6$ between the proximal apex 450 and the central apex 440. Such a state may be generally referred to as an expanded state or unstressed state of the suture-fastening device 400. In at least one example, the suture-fastening device 400 may be moved from the default state illustrated in FIG. 4A to the expanded state illustrated in FIG. 4B by applying a force to the proximal loop portion 420.

A compressive force applied to the proximal loop portion 420 constricts the proximal loop portion 420 to shorten the distance $d_6$ between the proximal apex 450 and Lithe central apex 440. As previously introduced, the distal loop portion 410 and the proximal loop portion 420 are part of a continuous piece. Accordingly, as the proximal loop portion 420 is constricted, the distal loop portion 410 expands.

It may be desirable to move the distal loop portion 410 to the expanded state to facilitate the introduction of a suture into the suture-fastening device 400 as well as to facilitate the advancement of the suture-fastening device 400 over a suture into proximity with a puncture in the tissue. The deployment device 500 may be used to selectively expand the suture-fastening device 400 and to introduce the suture-fastening device 400 for deployment, as will now be discussed in more detail.

Figure 5A:
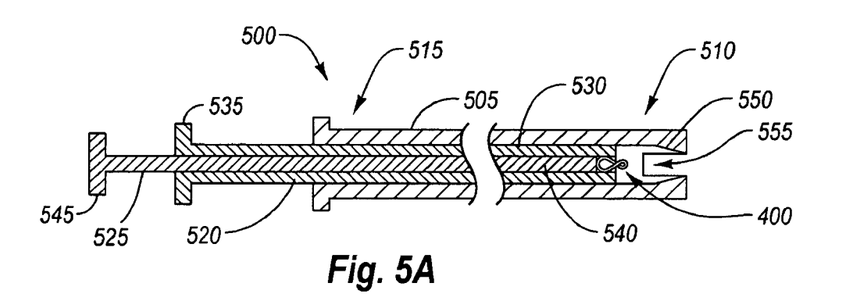
FIG. 5A illustrates a partial cross-sectional view of the system of FIG. 3 in which the suture-fastening device is in a default state.

FIG. 5A illustrates a cross-sectional view of the deployment device 500, according to one example. The deployment device 500 includes a housing 505 having a distal portion 510 and a proximal portion 515. The deployment device 500 further includes a first actuator 520 and a second actuator 525. In the illustrated example, the first and second actuators 520, 525 are arranged in a nested fashion within the housing 505 such that the first actuator 520 is located within the housing 505 and the second actuator 525 is nested within the first actuator 520.

The first actuator 520 includes a first plunger portion 530 and a handle portion 535. The second actuator 525 also includes a second plunger portion 540 and a handle portion 545.

The first plunger portion 530 of the first actuator 520 is configured to house the suture-fastening device 400 before deployment, as illustrated in FIG. 5A, and to cooperate with other parts of the deployment device to move the suture-fastening device 400 to an expanded state and deploy the suture-fastening device 400. In at least one example, the housing 505 includes a differentially sized lumen that cooperates with the first and second actuators 520, 525 to move the suture-fastening device 400 to the expanded state.

In particular, the distal portion 510 of the housing 505 may include a necked portion 550 in which the diameter of the lumen defined in the distal portion 510 transitions from a first diameter to a second diameter, the second diameter being smaller than the first diameter. In the illustrated example, the first actuator 520 and the second actuator 525 initially move together relative to the housing 505. As a result, advancing handle portions 535, 545 distally causes the second plunger portion 540 and the first plunger portion 530 to translate distally relative to the housing 505.

Figure 5B:
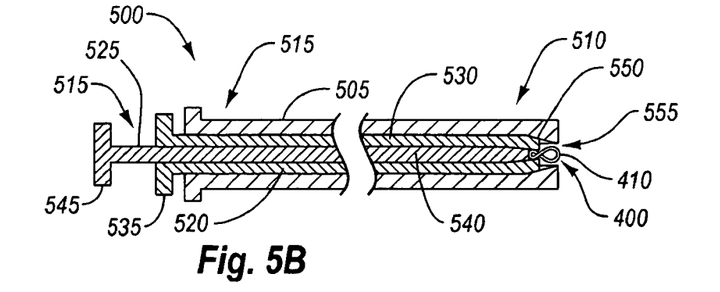
FIG. 5B illustrates a partial cross-sectional view of the system of FIG. 5A in which the suture-fastening device is in a pre-deployed state.

As illustrated in FIG. 5B, as the first plunger portion 530 is advanced distally, the first plunger portion 530 engages the necked portion 550. The engagement between the first plunger portion 530 and the necked portion 550 constricts the second plunger portion 540. The constriction of the second plunger portion 540 constricts the proximal loop portion 420. As previously introduced, constriction of the proximal loop portion 420 causes the distal loop portion 410 to expand.

Figure 5C:
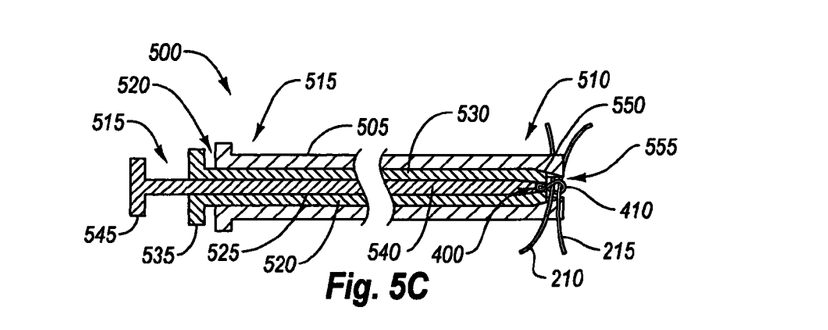
FIG. 5C illustrates a partial cross-sectional view of the system of FIG. 5A in which ends of a suture are threaded through a window in the deployment device and through the suture-fastening device.

The distal portion 510 of the housing 505 includes a slot 555 defined therein. As the first and second actuators 520, 525 advance as described above to constrict the proximal loop portion 420 and expand the distal loop portion 410, the advancement can bring the then expanded distal loop portion 410 into communication with the slot 555. As illustrated in FIG. 5C, thus positioning the distal loop portion 410 in an expanded state proximate the slot 555 can allow ends 210, 215 of suture 205 to be threaded through the slot 555 and the distal loop portion 410.

Figure 5D:
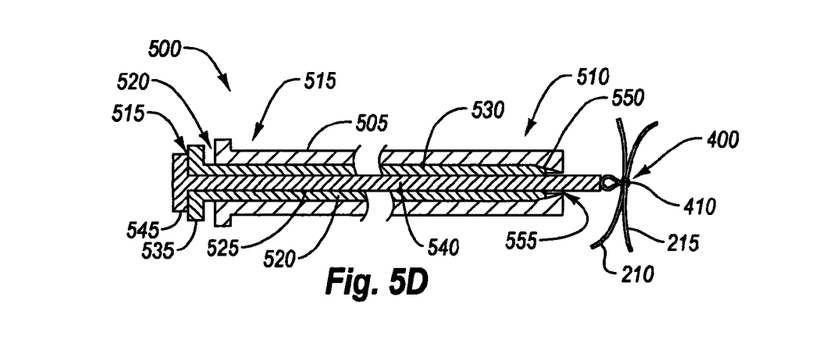
FIG. 5D illustrates a partial cross-sectional view of engagement between the suture-fastening device and a suture as the suture-fastening device is deployed.

Once the ends 210, 215 of suture 205 have been threaded through the slot 555 and the distal loop portion 410, the deployment device 500 may be moved to place the suture-fastening device 400 at a desired location, such as proximate a puncture. Thereafter, the second actuator 525 may be advanced distally relative to both the first actuator 520 and the housing 505. As the second actuator 525 advances distally, the second actuator 525 drives the suture-fastening device 400 as well until the suture-fastening device 400 is deployed from the distal portion 510 of the deployment device 500, as illustrated in FIG. 5D.

When deployed, the suture-fastening device 400 may move toward the default state described above with reference to FIG. 4A, such that the distal loop portion 410 constricts about the ends 210, 215 of suture 205. As the distal loop portion 410 constricts about the ends 210, 215 of suture 205, the distal loop portion 410 secures the position of the suture 205 relative to a puncture (e.g., P FIGS. 2A-2D), as described above. The ends 210, 215 of suture 205 may then be severed proximally of the suture-fastening device 400.

After the ends 210, 215 have been severed, the suture-fastening device 400 maintains and/or provides tension in the rest of suture 205 to maintain and/or provide apposition in the puncture in which the suture 205 is deployed. Accordingly, a system, method, and device have been disclosed herein for maintaining apposition in a suture. The system, method and device described herein may allow a practitioner to rapidly secure apposition in a suture in a puncture.

Although discussion has been made to retaining or securing a single suture, it will be understood that the suture-fastening device may receive the ends of one or more sutures. This again would decrease the time to close a wound. To this point, a configuration has been described in which a looped portion of the device moves between a constricted and expanded state due to spring forces within a resilient material. Other configurations are possible in which a device moves from an expanded state to a constricted state to engage a suture. One such example will be now be discussed that, while in an expanded state, has a single looped portion, and, while in a constricted state, has two looped portions, each of which are smaller than the single looped portion of the expanded state.

Figure 6:
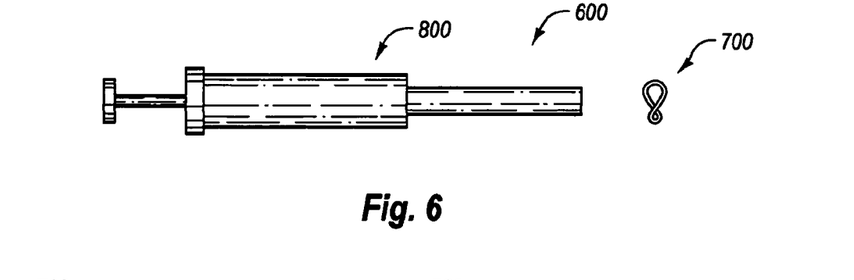
FIG. 6 illustrates a system for retaining a suture according to one example.

FIG. 6 illustrates a system 600 for securing a suture that includes a suture-fastening device 700 and a deployment device 800. As will be discussed in more detail below, the deployment device 800 is configured to deploy the suture-fastening device 700 to provide and/or maintain tension in a suture to thereby provide and/or maintain apposition in a puncture in tissue.

Figure 7A:
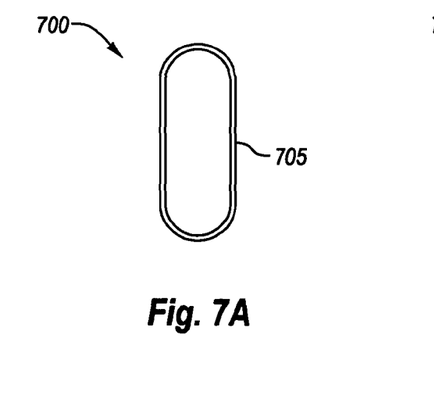
FIG. 7A illustrates another suture-fastening device in a pre-deployed state.

FIG. 7A illustrates the suture-fastening device 700 in a pre-deployed state. The suture-fastening device 700 illustrated is formed of a continuous strip. While the suture-fastening device 700 is described as a continuous loop, the suture-fastening device 700 may be formed of several different materials joined to form a closed loop. Further, in additional configurations, the suture-fastening device 700 forms an opened loop. In the state illustrated in FIG. 7A, the suture-fastening device 700 initially forms a single looped portion 705. Through the application and/or removal of forces, the single looped portion 705 can move to a constricted state.

Figure 7B:
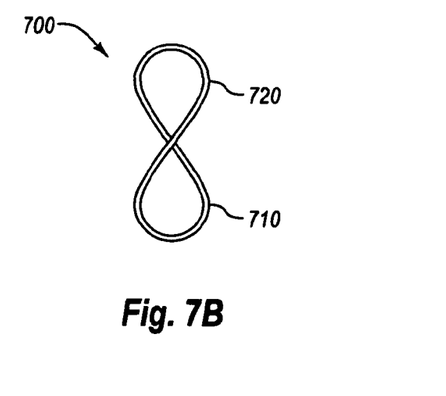
FIG. 7B illustrates the suture-fastening device of FIG. 7A in a deployed state.

FIG. 7B illustrates the suture-fastening device 700 in a deployed state in which the suture-fastening device 700 includes a distal looped portion 710 and a proximal looped portion 720. The suture-fastening device 700 may move between the pre-deployed state illustrated in FIG. 7A and the deployed state illustrated in FIG. 7B by a twisting movement. In one example, the deployed state of the suture-fastening device 700 illustrated in FIG. 7B is the default state. In such an example, a combination of forces may be applied to twist the suture-fastening device 700 to the configuration illustrated in FIG. 7A.

The deployment device 800 illustrated in more detail in FIGS. 8A-8D may be configured to move and/or maintain the suture-fastening device 700 in the pre-deployed state. The deployment device 800 includes a housing 805 having a distal portion 810 and a proximal portion 815. A lumen is defined in at least the distal portion 810 and can pass through both the distal portion 810 and the proximal portion 815. At least the distal portion 810 may be shaped to maintain the suture-deployment device 700 in a pre-deployed state.

Figure 8A:
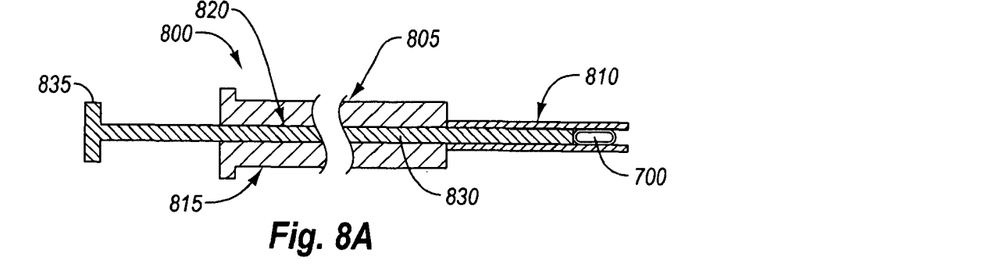
FIG. 8A illustrates a partial cross-sectional view of the system of FIG. 6 in which the suture-fastening device is in a default state.
Figure 8B:
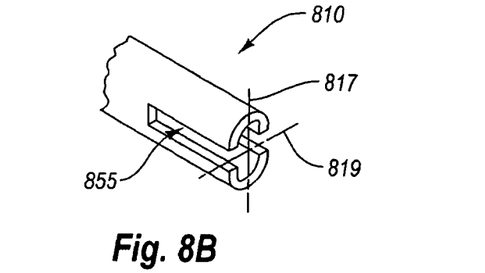
FIG. 8B illustrates a distal portion of a deployment device in more detail.

In particular, 8B illustrates a partial cross sectional view of the distal portion 810. As illustrated in FIG. 8B, the distal portion 810 may have a major axis 817 and a minor axis 819. The major axis 817 may approximately correspond in size to the diameter of the suture-fastening device 700 in the pre-deployed state. The minor axis 819 may approximately correspond in size to a thickness of the suture-fastening device 700.

Such a configuration allows the suture-fastening device 700 to be loaded into the distal portion 810 and to be maintained in the pre-deployed state. In at least one example, the distal portion 810 of the housing 805 includes a slot 855 defined therein. The suture-fastening device 700 may be loaded into the distal portion 810 of the housing 805 such that the suture-fastening device 700 is in communication with the slot 855.

Figure 8C:
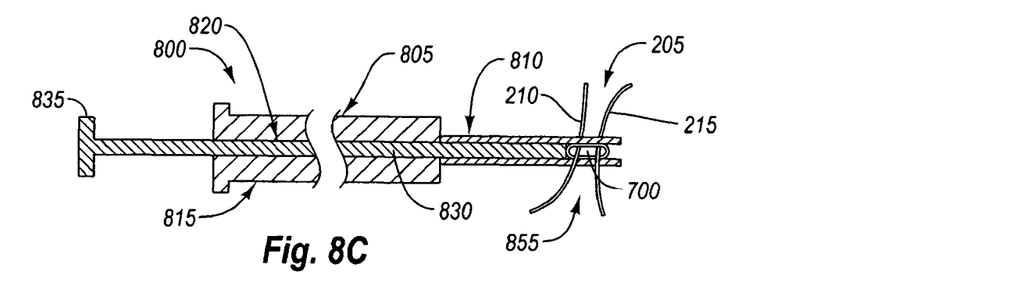
FIG. 8C illustrates a partial cross-sectional view of the system of FIG. 8A in which the suture-fastening device is in a pre-deployed state in which ends of a suture are threaded through a window in the deployment device and through the suture-fastening device.

As illustrated in FIG. 8C, while the suture-fastening device 700 is in communication with the slot 855, ends 210, 215 of suture 205 may be passed through both the slot 855 and the suture-fastening device 700. Accordingly, the deployment device 800 may facilitate the threading of suture 205 through the suture-fastening device 700 by maintaining the suture-fastening device 700 in an expanded state. With suture 205 thus loaded into the deployment device 800, the deployment device 800 may be moved to a deployment location, such as proximate a puncture that suture 205 have brought into apposition.

Returning again to FIG. 8A, the deployment device 800 further includes an actuator 820. The actuator 820 includes a plunger portion 830 and a handle portion 835. By moving the actuator 820, such as by moving the handle portion 835 toward the housing 805, the plunger portion 830 may drive the suture-fastening device 700 out of the distal portion 810 of the housing 805 to thereby deploy the suture-fastening device 700 with suture 205 threaded therethrough.

Figure 8D:
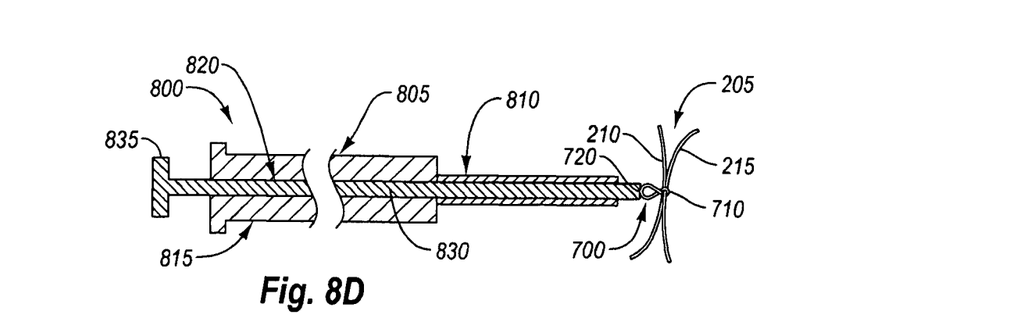
FIG. 8D illustrates a partial cross-sectional view of the system of FIG. 8A showing engagement between the suture-fastening device and a suture as the suture-fastening device is deployed.

As the suture-fastening device 700 is driven from the distal portion 810 as illustrated in FIG. 8D, the suture-fastening device 700 returns to the default state. In the illustrated example, the distal loop portion 710 may engage suture 205. Further, the distal loop portion 710 may be smaller relative to the proximal loop portion 720. In other examples, the distal loop portion 710 may be of the same size as the distal loop portion 710 in the default state. In still other examples, the distal loop portion 710 may be larger than the proximal loop portion 720 in the default state. Regardless of the configuration of the suture-fastening device 700, once the suture-fastening device 700 is released from the deployment device 800 the suture-fastening device 700 moves to a state in which at least one of the looped portions engages a suture to provide and/or maintain tension in the suture and/or to prevent the suture from relaxing.

In at least one example, the suture-fastening device may be formed from a shape memory material. In other examples, the suture-fastening device may be formed from a bio-resorbable material.

Accordingly, methods, devices, and systems have been provided herein for fastening a suture. In at least one example, a suture-fastening device can be used to retain and/or provide apposition for a suture that has been deployed to close an opening in tissue. The suture-fastening device includes at least a distal loop portion that moves from a constricted state having a first diameter to a constricted state having a second diameter, the second diameter being less than the first. In at least one example, the closure device includes also includes a proximal loop. The suture-fastening device may be moved from a single loop configuration in an expanded state to a configuration that includes a proximal loop and a constricted distal loop in a constricted state. In another example, a suture-fastening device is provided in which the diameter of a distal loop decreases while the diameter of a proximal loop increases as the suture-fastening device is deployed.

Figure 9A:
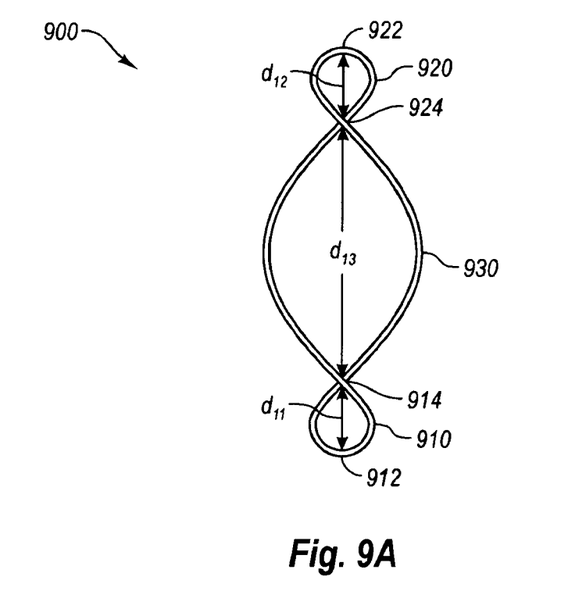
FIG. 9A illustrates another suture-fastening device in a pre-deployed state.
Figure 9B:
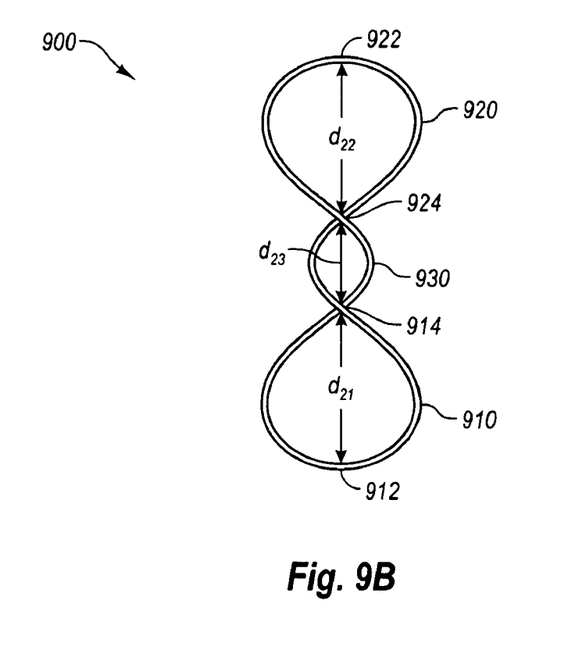
FIG. 9B illustrates the suture-fastening device of FIG. 9A in a deployed state.

FIGS. 9A and 9B illustrate an additional example suture-fastening device 900 in accordance with an implementation of the present disclosure. In the illustrated example, the suture-fastening device 900 has a proximal loop portion 920, a distal loop portion 910, and a central loop portion 930 that are in communication with each other.

FIG. 9A illustrates the suture-fastening device 900 in a pre-deployed state. Such a state may be referred to as a default state or a stressed state. The distal loop portion 910 includes a distal apex 912 as well as a distal central apex 914. The proximal loop portion 920 includes a proximal apex 922 and a proximal central apex 924. In the illustrated example, the distal loop portion 910, the proximal loop portion 920, and the central loop portion 930 may be formed of a substantially continuous piece of material.

The distal apex 912 and the distal central apex 914 are separated by a distance referred to as $d_{11}$ while the proximal apex 922 and proximal distal apex 924 are separated by a distance referred to as $d_{12}$, and the distal central apex 914 and proximal central apex 924 are separated by a distance referred to as $d_{13}$. The distances $d_{11}$, $d_{12}$, and $d_{13}$ are provided for ease of illustration only and not by way of limitation. In the default state, distances $d_{11}$ and $d_{12}$ may be less than distance $d_{13}$.

In the illustrated example the distal loop portion 910, the proximal loop portion 920, and the central loop portion 930 are formed from a single continuous piece. For instance, the suture-fastening device 900 can be cut or removed from a single piece of material as a generally circular or ovular configuration and then be heat set or annealed to transition from the configuration illustrated in FIG. 9A to that of FIG. 9B. As a result, a change in the size of one of loop portions results in a change in size of the other loop portions, as will be discussed in more detail below.

FIG. 9B illustrates the suture-fastening device 900 in a state in which central loop portion 930 is constricted while the distal loop portion 910 and the proximal loop portion 920 are expanded. In such a state, the distance $d_{21}$ between the distal apex 912 and the distal central apex 914 and the distance $d_{22}$ between the proximal apex 922 and the proximal central apex 924 are greater than the distance $d_{23}$ between the proximal central apex 924 and the distal central apex 914. Such a state may be generally referred to as an expanded state or unstressed state of the suture-fastening device 900. In at least one example, the suture-fastening device 900 may be moved from the default state illustrated in FIG. 9A to the expanded state illustrated in FIG. 9B by applying a force to the proximal loop portion 920.

A compressive force applied to the proximal loop portion 920 constricts the proximal loop portion 920 to shorten the distance $d_6$ between the proximal apex 950 and the central apex 940. As previously introduced, the distal loop portion 910 and the proximal loop portion 920 are part of a continuous piece. Accordingly, as the proximal loop portion 920 is constricted, the distal loop portion 910 expands.

It may be desirable to move the distal loop portion 910 to the expanded state to facilitate the introduction of a suture into the suture-fastening device 900 as well as to facilitate the advancement of the suture-fastening device 900 over a suture into proximity with a puncture in the tissue. The deployment device 500 may be used to selectively expand the suture-fastening device 900 and to introduce the suture-fastening device 900 for deployment, as will now be discussed in more detail.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A system for maintaining apposition in a suture, the system comprising:
   a deployment device, the deployment device having a housing and an actuator assembly; and
   a suture-fastening device, the suture-fastening device having a looped body, the looped body having a first looped portion having a first apex and a second central apex disposed in a central portion of the looped body, the central portion of the looped body having an overlapping configuration at the second central apex with one portion of the looped body transversely crossing another portion of the looped body, the first apex and the second central apex being separated by a first distance while the suture-fastening device is in a pre-deployed state and being configured to resiliently move to a deployed state in which the first apex and the second central apex are separated by a second distance, the first distance being greater than the second distance,
   wherein the deployment device is configured to move the suture-fastening device from the deployed state to the pre-deployed state to thread the suture through the suture-fastening device and then deploy the suture-fastening device which returns to the deployed state to maintain apposition in the suture.

2. The system of claim 1, wherein the suture-fastening device further includes a second looped portion having a third apex, the second and third apexes being separated by a third distance in a pre-deployed state and a fourth distance in a deployed state, the fourth distance being greater than the third distance and wherein the deployment device is configured to selectively apply a force to the second looped portion to move the suture-fastening device to the pre-deployed state.

3. The system of claim 1, wherein the actuator assembly includes a first actuator having a first plunger portion and a second actuator having and a second plunger portion, the first plunger being located at least partially within the housing and the second plunger portion being located at least partially within the first plunger, wherein the first plunger is configured to cooperate with the housing to move the suture-fastening device to the pre-deployed state and wherein the second plunger portion is configured to deploy the suture-fastening device from a distal end of the deployment device.

4. The system of claim 3, wherein the first actuator further comprises a first handle portion operatively associated with the first plunger and a second handle portion operatively associated with the second plunger portion wherein actuation of the first handle portion moves the suture-fastening device to a pre-deployed state and wherein actuation of the second handle portion deploys the suture-fastening device from a distal end of the deployment device.

5. The system of claim 1, wherein the looped body is configured to move between a pre-deployed state in which the first looped portion forms a single loop and a deployed state in which the looped body forms a plurality of looped portions, wherein the housing is configured to maintain the suture-fastening device in the pre-deployed state.

6. The system of claim 5, wherein a distal end of the housing includes a major axis and a minor axis, the major axis being greater than a diameter of the first looped portion in the pre-deployed state.

7. The system of claim of claim 1, wherein the actuator assembly includes an actuator having a plunger portion operatively associated with a handle portion, the plunger portion being configured to deploy the suture-fastening device from a distal end of the housing in response to movement of the plunger portion.

8. A system for maintaining apposition in a suture, the system comprising:
   a deployment device, the deployment device having a housing and an actuator assembly; and
   a suture-fastening device, the suture-fastening device having a biased and continuous, closed looped body, the looped body having a first looped portion having a first apex and a second central apex disposed in a central portion of the looped body, the central portion of the looped body having an overlapping configuration at the second central apex with one portion of the looped body transversely crossing another portion of the looped body, the first apex and the second central apex being separated by a first distance while the suture-fastening device is in a pre-deployed state and being configured to resiliently move to a deployed state in which the first apex and the second central apex are separated by a second distance, the first distance being greater than the second distance, the looped body being biased to transition from the pre-deployed state to the deployed state, wherein the deployment device is configured to move the suture-fastening device from the pre-deployed state to the deployed state.

9. The system of claim 8, wherein the actuator assembly includes a first actuator having a first plunger portion and a second actuator having and a second plunger portion, the first plunger being located at least partially within the housing and the second plunger portion being located at least partially within the first plunger, wherein the first plunger is configured to cooperate with the housing to move the suture-fastening device to the pre-deployed state and wherein the second plunger portion is configured to deploy the suture-fastening device from a distal end of the deployment device.

10. The system of claim 9, wherein the first actuator further comprises a first handle portion operatively associated with the first plunger and a second handle portion operatively associated with the second plunger portion wherein actuation of the first handle portion moves the suture-fastening device to a pre-deployed state and wherein actuation of the second handle portion deploys the suture-fastening device from a distal end of the deployment device.

11. The system of claim 8, wherein the looped body is configured to move between a pre-deployed state in which the first looped portion forms a single loop and a deployed state in which the looped body forms a plurality of looped portions, wherein the housing is configured to maintain the suture-fastening device in the pre-deployed state.

12. The system of claim 11, wherein a distal end of the housing includes a major axis and a minor axis, the major axis being greater than a diameter of the first looped portion in the pre-deployed state.

13. The system of claim of claim 8, wherein the actuator assembly includes an actuator having a plunger portion operatively associated with a handle portion, the plunger portion being configured to deploy the suture-fastening device from a distal end of the housing in response to movement of the plunger portion.

14. A system for maintaining apposition in a suture, the system comprising:
a deployment device, the deployment device having a housing, a lumen extending through the housing, and an actuator assembly slidable within the lumen, a distal end of the lumen having a necked configuration; and
a suture-fastening device, the suture-fastening device having a biased looped body, the looped body having a first looped portion having a first apex and a second central apex disposed in a central portion of the looped body, the central portion of the looped body having an overlapping configuration at the second central apex with one portion of the looped body transversely crossing another portion of the looped body, the first apex and the second central apex being separated by a first distance while the suture-fastening device is in a pre-deployed state and being configured to resiliently move to a deployed state in which the first apex and the second central apex are separated by a second distance, the first distance being greater than the second distance, the looped body being biased to transition from the pre-deployed state to the deployed state, wherein the deployment device is configured to move the suture-fastening device from the deployed state to the pre-deployed state to thread the suture through the suture-fastening device and then deploy the suture-fastening device which returns to the deployed state to maintain apposition in the suture.

15. The system of claim 14, wherein the actuator assembly includes a first actuator having a first plunger portion and a second actuator having and a second plunger portion, the first plunger being located at least partially within the housing and the second plunger portion being located at least partially within the first plunger, wherein the first plunger is configured to cooperate with the housing to move the suture-fastening device to the pre-deployed state and wherein the second plunger portion is configured to deploy the suture-fastening device from a distal end of the deployment device.

16. The system of claim 15, wherein the first actuator further comprises a first handle portion operatively associated with the first plunger and a second handle portion operatively associated with the second plunger portion wherein actuation of the first handle portion moves the suture-fastening device to a pre-deployed state and wherein actuation of the second handle portion deploys the suture-fastening device from a distal end of the deployment device.

17. The system of claim 14, wherein the looped body is configured to move between a pre-deployed state in which the first looped portion forms a single loop and a deployed state in which the looped body forms a plurality of looped portions, wherein the housing is configured to maintain the suture-fastening device in the pre-deployed state.

18. The system of claim 17, wherein a distal end of the housing includes a major axis and a minor axis, the major axis being greater than a diameter of the first looped portion in the pre-deployed state.

19. The system of claim of claim 14, wherein the actuator assembly includes an actuator having a plunger portion operatively associated with a handle portion, the plunger portion being configured to deploy the suture-fastening device from a distal end of the housing in response to movement of the plunger portion.

* * * * *